US012735752B2

(12) United States Patent
Kosmicki et al.

(10) Patent No.: US 12,735,752 B2
(45) Date of Patent: Sep. 15, 2026

(54) METHODS OF IDENTIFYING SUBJECTS HAVING AN INCREASED RISK OF DEVELOPING A CORONAVIRUS INFECTION AND TREATMENT THEREOF

(71) Applicant: Regeneron Pharmaceuticals, Inc., Tarrytown, NY (US)

(72) Inventors: Jack Kosmicki, Tarrytown, NY (US); Julie Horowitz, Tarrytown, NY (US); Manuel Allen Revez Ferreira, Tarrytown, NY (US); Goncalo Abecasis, Tarrytown, NY (US); Aris Baras, Tarrytown, NY (US); Amy Damask, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1256 days.

(21) Appl. No.: 17/541,602

(22) Filed: Dec. 3, 2021

(65) Prior Publication Data

US 2022/0177982 A1 Jun. 9, 2022

Related U.S. Application Data

(60) Provisional application No. 63/121,067, filed on Dec. 3, 2020.

(51) Int. Cl.

| | |
|---|---|
| ***C12Q 1/6888*** | (2018.01) |
| ***C12Q 1/6883*** | (2018.01) |
| ***C12Q 1/70*** | (2006.01) |
| *C07K 16/104* | (2026.01) |

(52) U.S. Cl.
CPC ......... *C12Q 1/6888* (2013.01); *C12Q 1/6883* (2013.01); *C12Q 1/701* (2013.01); *C07K 16/104* (2026.01); *C12Q 2600/112* (2013.01); *C12Q 2600/156* (2013.01)

(58) Field of Classification Search
None
See application file for complete search history.

(56) References Cited

U.S. PATENT DOCUMENTS

2019/0345566 A1 11/2019 Khera et al.

FOREIGN PATENT DOCUMENTS

WO WO-2021237292 A1 * 12/2021 ............. G16H 50/30

OTHER PUBLICATIONS

Pairo-Castineira et al., medRxiv, Sep. 25, 2020, https://www.medrxiv.org/content/10.1101/2020.09.24.20200048v2. (Year: 2020).*
Zhu et al., "Association of obesity and its genetic predisposition with the risk of severe COVD-19: Analysis of population-based cohort data", Metabolism, Clinical and Experimental, 2020, 112, pp. 1-7.
Ellinghaus et al., "Genoewide Association Study of Severe Covid-19 with Respiratory Failure", The New England Journal of Medicine, 2020, 383(16), pp. 1522-1534.

* cited by examiner

*Primary Examiner* — Nicole Kinsey White
(74) *Attorney, Agent, or Firm* — Armstrong Teasdale LLP

(57) ABSTRACT

Methods of treating subjects having a coronavirus infection, and methods of identifying subjects having an increased risk of a coronavirus infection are provided herein.

17 Claims, 15 Drawing Sheets

| Number of established risk factors* | Risk among COVID-19 cases in UKB study (N positive and [hospitalized or severe] / N positive) | | Unadjusted Risk Difference | Odds Ratio** | | |
|---|---|---|---|---|---|---|
| | Top 10% GRS | Rest of Population | | Estimate (95% CI) | SE | P-value |
| Risk of hospitalization | | | | | | |
| 0 | 48.57 (17/35) | 33.83 (90/266) | 14.74 | 1.74 (0.82-3.65) | 0.378 | 0.145 |
| 1 | 68.97 (40/58) | 52.30 (216/413) | 16.67 | 2.08 (1.15-3.88) | 0.309 | 0.018 |
| 2 | 73.53 (25/34) | 67.82 (255/376) | 5.71 | 1.34 (0.62-3.16) | 0.413 | 0.480 |
| 3+ | 86.79 (46/53) | 81.14 (456/562) | 5.65 | 1.57 (0.72-3.91) | 0.424 | 0.291 |
| Risk of severe disease | | | | | | |
| 0 | 14.29 (5/35) | 7.89 (21/266) | 6.39 | 1.44 (0.39-4.32) | 0.601 | 0.547 |
| 1 | 34.48 (20/58) | 18.89 (78/413) | 15.6 | 2.32 (1.23-4.31) | 0.319 | 0.008 |
| 2 | 35.29 (12/34) | 28.46 (107/376) | 6.84 | 1.35 (0.62-2.56) | 0.389 | 0.435 |
| 3+ | 47.17 (25/53) | 36.30 (204/562) | 10.87 | 1.58 (0.88-2.84) | 0.296 | 0.120 |

* Age ≥ 65, Male, BMI > 30 (obese), plus any risk factor/comorbidity that had an age/sex adjusted nominal p-value < 0.1 in an analysis evaluating hospitalized yes/no or severe yes/no by risk factor, which included Current Smoking, Diabetes, Hypertension, Cardiovascular Disease, Chronic Kidney Disease, Liver Disease, and COPD.

** Logistic regression model adjusted for ancestry-informative PCs.

Figure 1

| Demographic | COVID-19 Positive | | Covid-19 Negative or Unknown |
|---|---|---|---|
| | Hospitalized | Not Hospitalized | |
| **UK Biobank** | | | |
| Total N | 1424 | 1816 | 470737 |
| Average Age, y (% >60y) | 62.0 (58.0%) | 50.0 (22.0%) | 57.0 (36%) |
| Gender, n (% Female) | 573 (40.0%) | 994 (54.0%) | 260336 (55.3%) |
| Hypertension, n (%) | 665 (46.7%) | 421 (23.1%) | 109611 (23.2%) |
| Cardiovascular Disease, n (%) | 256 (17.9%) | 136 (9.0%) | 31542 (6.7%) |
| Type 2 Diabetes, n (%) | 267 (18.7%) | 141 (7.8%) | 28983 (6.1%) |
| Chronic kidney disease, n (%) | 112 (7.8%) | 44 (2.4%) | 9162 (1.9%) |
| Asthma, n (%) | 302 (16.7%) | 229 (16.1%) | 67019 (14.2%) |
| COPD, n (%) | 150 (10.5%) | 56 (3.1%) | 11656 (2.4%) |
| **GHS** | | | |
| Total N | 179 | 760 | 121448 |
| Average Age, y (% >60y) | 65.8 (71.5%) | 53.6 (36.4%) | 55.2 (42.7%) |
| Gender, n (% Female) | 101 (56.4%) | 510 (67.1%) | 76314 (62.8%) |
| Hypertension, n (%) | 138 (77.1%) | 381 (50.1%) | 58857 (48.5%) |
| Cardiovascular Disease, n (%) | 76 (42.5%) | 117 (15.4%) | 18580 (15.3%) |
| Type 2 Diabetes, n (%) | 77 (43.0%) | 177 (23.3%) | 26200 (21.6%) |
| Chronic kidney disease, n (%) | 69 (38.5%) | 104 (13.7%) | 15584 (12.8%) |
| Asthma, n (%) | 16 (8.9%) | 59 (7.78%) | 7839 (6.5%) |
| COPD, n (%) | 49 (27.4%) | 73 (9.6%) | 11802 (9.7%) |
| **PMBB** | | | |
| Total N | 75 | 103 | 16158 |
| Average Age, y (% >60y) | 63.2 (64.0%) | 48.3 (21.4%) | 63.0 (61.2%) |
| Gender, n (% Female) | 42 (56.0%) | 74 (71.8%) | 8430 (52.2%) |
| Hypertension, n (%) | 66 (88.0%) | 54 (52.4%) | 10590 (65.5%) |
| Cardiovascular Disease, n (%) | 46 (61.3%) | 19 (18.5%) | 6951 (43.0%) |
| Type 2 Diabetes, n (%) | 51 (68%) | 32 (31.1%) | 4909 (30.4%) |
| Chronic kidney disease, n (%) | 44 (58.7%) | 14 (13.6%) | 3831 (23.7%) |
| Asthma, n (%) | 19 (25.3%) | 23 (22.3%) | 2342 (14.5%) |
| COPD, n (%) | 21 (28.0%) | 9 (8.7%) | 2095 (13.0%) |

Figure 2

| Broad phenotype category | Phenotype | Case/control group | Definition | | |
|---|---|---|---|---|---|
| | | | COVID-19 status | Hospitalized | Severe disease* |
| Risk of infection | COVID-19 positive vs. COVID-19 negative or unknown | Cases | Positive | - | - |
| | | Controls | Negative or unknown | No or NA | No or NA |
| | COVID-19 positive vs. COVID-19 negative | Cases | Positive | - | - |
| | | Controls | Negative | No or NA | No or NA |
| | COVID-19 positive and not hospitalized vs. COVID-19 negative or unknown | Cases | Positive | No | No |
| | | Controls | Negative or unknown | No or NA | No or NA |
| | COVID-19 positive and hospitalized vs. COVID-19 negative or unknown | Cases | Positive | Yes (or death**) | - |
| | | Controls | Negative or unknown | No or NA | No or NA |
| | COVID-19 positive and severe vs. COVID-19 negative or unknown | Cases | Positive | - | Yes |
| | | Controls | Negative or unknown | No or NA | No or NA |
| Risk of adverse outcomes amongst infected individuals | COVID-19 positive and hospitalized vs. COVID-19 positive and not hospitalized | Cases | Positive | Yes (or death**) | - |
| | | Controls | Positive | No | No |
| | COVID-19 positive and severe vs. COVID-19 positive and not hospitalized | Cases | Positive | - | Yes |
| | | Controls | Positive | No | No |
| | COVID-19 positive and hospitalized vs. COVID-19 positive, not hospitalized, comorbidities and age>60 | Cases | Positive | Yes (or death**) | - |
| | | Controls | Positive with co-morbidities and age>60 | No | No |

Figure 3

| Broad phenotype category | Phenotype | Case/control group | Sample size with genetic data | | | |
|---|---|---|---|---|---|---|
| | | | UK Biobank | GHS | PMBB | Total |
| Risk of infection | COVID-19 positive vs. COVID-19 negative or unknown | Cases | 2003 | 854 | 166 | 3023 |
| | | Controls | 453,835 | 112,877 | 8738 | 575450 |
| | COVID-19 positive vs. COVID-19 negative | Cases | 2003 | 854 | 166 | 3023 |
| | | Controls | 15,653 | 16,148 | 959 | 32760 |
| | COVID-19 positive and not hospitalized vs. COVID-19 negative or unknown | Cases | 735 | 689 | 99 | 1523 |
| | | Controls | 453,835 | 112,877 | 8738 | 575450 |
| | COVID-19 positive and hospitalized vs. COVID-19 negative or unknown | Cases | 1268 | 165 | 67 | 1500 |
| | | Controls | 453,835 | 112,877 | 8738 | 575450 |
| | COVID-19 positive and severe vs. COVID-19 negative or unknown | Cases | 504 | 36 | NA | 540 |
| | | Controls | 443,343 | 112,877 | NA | 556220 |
| Risk of adverse outcomes amongst infected individuals | COVID-19 positive and hospitalized vs. COVID-19 positive and not hospitalized | Cases | 1145 | 165 | 67 | 1377 |
| | | Controls | 652 | 689 | 99 | 1440 |
| | COVID-19 positive and severe vs. COVID-19 positive and not hospitalized | Cases | 472 | 36 | NA | 508 |
| | | Controls | 652 | 689 | NA | 1341 |
| | COVID-19 positive and hospitalized vs. COVID-19 positive, not hospitalized, comorbidities and age>60 | Cases | 1145 | 165 | NA | 1310 |
| | | Controls | 189 | 125 | NA | 314 |

Figure 3 (cont.)

| Locus_index | Independent signal index | Reference | First author | Phenotype |
|---|---|---|---|---|
| 1 | 1 | world wide web at medrxiv.org/content/10.1101/2020.09.24.20200048v2 | Pairo-Castineira | covid19_severe_vs_negative_or_unknown |
| 1 | 2 | world wide web at medrxiv.org/content/10.1101/2020.09.04.20188318v1 | Shelton | covid_test_positive_vs_negative |
| 2 | 1 | world wide web at medrxiv.org/content/10.1101/2020.09.24.20200048v2 | Pairo-Castineira | covid19_severe_vs_negative_or_unknown |
| 3 | 1 | world wide web at medrxiv.org/content/10.1101/2020.09.04.20188318v1 | Shelton | covid_test_positive_vs_negative |
| 4 | 1 | world wide web at medrxiv.org/content/10.1101/2020.09.24.20200048v2 | Pairo-Castineira | covid19_severe_vs_negative_or_unknown |
| 5 | 1 | world wide web at medrxiv.org/content/10.1101/2020.09.24.20200048v2 | Pairo-Castineira | covid19_severe_vs_negative_or_unknown |
| 6 | 1 | world wide web at medrxiv.org/content/10.1101/2020.09.24.20200048v2 | Pairo-Castineira | covid19_severe_vs_negative_or_unknown |
| 7 | 1 | world wide web at medrxiv.org/content/10.1101/2020.09.24.20200048v2 | Pairo-Castineira | covid19_severe_vs_negative_or_unknown |

Pairo-Castineira: Six variants from their Table 2 (main results) and 3 (replication), takin only top variant per locus Shelton: Two variants from the two loci that they call out in the paper (chr3 and ABO). Other variants called out as potentially false-positives, all (or nearly all) discovered in analyses with <1000 cases

Figure 4

| Locus_index | Independent signal index | rsID | hg38_CPRA | Nearest gene | Effect_allele | Locus | Odds_Ratio |
|---|---|---|---|---|---|---|---|
| 1 | 1 | rs73064425 | 3:45859597:C:T | LZTFL1 | T | 3p21.31 | 2.14 |
| 1 | 2 | rs2531743 | 3:45796808:G:A | SLC6A20 | G | 3p21.31 | 0.917 |
| 2 | 1 | rs143334143 | 6:31153649:G:A | CCHCR1 | A | 6p21.33 | 1.85 |
| 3 | 1 | rs9411378 | 9:133270015:A:C | ABO | C | 9q34.2 | 0.857 |
| 4 | 1 | rs10735079 | 12:112942203:G:A | OAS3 | A | 12q24.13 | 1.29 |
| 5 | 1 | rs2109069 | 19:4719431:G:A | DPP9 | A | 19p13.3 | 1.36 |
| 6 | 1 | rs74956615 | 19:10317045:T:A | RAVER1 | A | 19p13.2 | 1.59 |
| 7 | 1 | rs2236757 | 21:33252612:A:G | IFNAR2 | A | 21q22.1 | 1.28 |

Pairo-Castineira: Six variants from their Table 2 (main results) and 3 (replication), takin only top variant per locus Shelton: Two variants from the two loci that they call out in the paper (chr3 and ABO). Other variants called out as potentially false-positives, all (or nearly all) discovered in analyses with <1000 cases

Figure 4 (cont.)

| Locus_index | Independent signal index | LCI | UCI | P_value | N_cases | N_controls | Chr | BP | Top independent association in locus |
|---|---|---|---|---|---|---|---|---|---|
| 1 | 1 | 1.88 | 2.45 | 4.77E-30 | 1676 | 8380 | 3 | 45859597 | 1 |
| 1 | 2 | 0.89 | 0.94 | 7.60E-10 | 12972 | 101268 | 3 | 45796808 | 1 |
| 2 | 1 | 1.61 | 2.13 | 8.82E-18 | 1676 | 8380 | 6 | 31153649 | 1 |
| 3 | 1 | 0.83 | 0.89 | 5.30E-20 | 12972 | 101268 | 9 | 133270015 | 1 |
| 4 | 1 | 1.18 | 1.42 | 1.65E-08 | 1676 | 8380 | 12 | 112942203 | 1 |
| 5 | 1 | 1.25 | 1.48 | 3.98E-12 | 1676 | 8380 | 19 | 4719431 | 1 |
| 6 | 1 | 1.35 | 1.87 | 2.31E-08 | 1676 | 8380 | 19 | 10317045 | 1 |
| 7 | 1 | 1.17 | 1.41 | 5.00E-08 | 1676 | 8380 | 21 | 33252612 | 1 |

Pairo-Castineira: Six variants from their Table 2 (main results) and 3 (replication), takin only top variant per locus
Shelton: Two variants from the two loci that they call out in the paper (chr3 and ABO). Other variants called out as potentially false-positives, all (or nearly all) discovered in analyses with <1000 cases

Figure 4 (cont.)

| Population | PRS Group | Risk of hospitalization among COVID-19 cases (N positive and hospitalized / N positive) | | Unadjusted Risk Difference |
|---|---|---|---|---|
| | | Highest GRS group | Rest of Population | |
| GHS EUR | Top 40% vs Rest of population | 17.54 (60/342) | 20.51 (105/512) | -2.96 |
| | Top 30% vs Rest of population | 19.14 (49/256) | 19.40 (116/598) | -0.26 |
| | Top 20% vs Rest of population | 22.22 (38/171) | 18.59 (127/683) | 3.63 |
| | Top 10% vs Rest of population | 23.26 (20/86) | 18.88 (145/768) | 4.38 |
| | Top 5% vs Rest of population | 25.58 (11/43) | 18.99 (154/811) | 6.59 |
| UKB EUR | Top 40% vs Rest of population | 66.20 (476/719) | 62.06 (669/1078) | 4.14 |
| | Top 30% vs Rest of population | 67.72 (365/539) | 62.00 (780/1258) | 5.71 |
| | Top 20% vs Rest of population | 71.11 (256/360) | 61.86 (889/1437) | 9.25 |
| | Top 10% vs Rest of population | 71.11 (128/180) | 62.89 (1017/1617) | 8.22 |
| | Top 5% vs Rest of population | 77.78 (70/90) | 62.98 (1075/1707) | 14.8 |

* GHS: Logistic regression model adjusted for age, sex, BMI, smoking status, hypertension, CKD and ancestry-informative PCs. UKB (European ancestry): Logistic regression model adjusted for age, sex, BMI, smoking status, hypertension, COPD, ancestry-informative PCs and REGENIE genome-wide predictor.

Figure 5

| Population | PRS Group | Risk of hospitalization among COVID-19 cases (N positive and hospitalized / N positive) | | Unadjusted Risk Difference |
|---|---|---|---|---|
| | | Highest GRS group | Rest of Population | |
| UKB SAS | Top 40% vs Rest of population | 58.33 (21/36) | 50.91 (28/55) | 7.42 |
| | Top 30% vs Rest of population | 57.14 (16/28) | 52.38 (33/63) | 4.76 |
| | Top 20% vs Rest of population | 50.00 (9/18) | 54.79 (40/73) | -4.79 |
| | Top 10% vs Rest of population | 66.67 (6/9) | 52.44 (43/82) | 14.23 |
| | Top 5% vs Rest of population | 60.00 (3/5) | 53.49 (46/86) | 6.51 |
| UKB AFR | Top 40% vs Rest of population | 56.52 (26/46) | 69.57 (48/69) | -13.04 |
| | Top 30% vs Rest of population | 48.57 (17/35) | 71.25 (57/80) | -22.68 |
| | Top 20% vs Rest of population | 52.17 (12/23) | 67.39 (62/92) | -15.22 |
| | Top 10% vs Rest of population | 75.00 (9/12) | 63.11 (65/103) | 11.89 |
| | Top 5% vs Rest of population | 83.33 (5/6) | 63.30 (69/109) | 20.03 |
| PMBB AFR | Top 40% vs Rest of population | 43.94 (29/66) | 38.00 (38/100) | 5.94 |
| | Top 30% vs Rest of population | 44.00 (22/50) | 38.79 (45/116) | 5.21 |
| | Top 20% vs Rest of population | 42.42 (14/33) | 39.85 (53/133) | 2.57 |
| | Top 10% vs Rest of population | 41.18 (7/17) | 40.27 (60/149) | 0.91 |
| | Top 5% vs Rest of population | 44.44 (4/9) | 40.13 (63/157) | 4.32 |

* GHS: Logistic regression model adjusted for age, sex, BMI, smoking status, hypertension, CKD and ancestry-informative PCs. UKB (European ancestry): Logistic regression model adjusted for age, sex, BMI, smoking status, hypertension, COPD, ancestry-informative PCs and REGENIE genome-wide predictor.

Figure 5 (cont.)

| Population | PRS Group | Adjusted Odds Ratio* | | | | |
|---|---|---|---|---|---|---|
| | | Estimate | SE | LCI | UCI | P-value |
| GHS EUR | Top 40% vs Rest of population | 1.16 | 0.236 | 0.73 | 1.84 | 0.536 |
| | Top 30% vs Rest of population | 1.39 | 0.250 | 0.85 | 2.27 | 0.187 |
| | Top 20% vs Rest of population | 1.73 | 0.279 | 0.99 | 2.98 | 0.05 |
| | Top 10% vs Rest of population | 1.67 | 0.361 | 0.81 | 3.35 | 0.158 |
| | Top 5% vs Rest of population | 2.06 | 0.468 | 0.8 | 5.05 | 0.123 |
| UKB EUR | Top 40% vs Rest of population | 1.23 | 0.124 | 0.96 | 1.57 | 0.097 |
| | Top 30% vs Rest of population | 1.42 | 0.133 | 1.09 | 1.84 | 9.20E-03 |
| | Top 20% vs Rest of population | 1.69 | 0.156 | 1.25 | 2.3 | 8.00E-04 |
| | Top 10% vs Rest of population | 1.82 | 0.213 | 1.21 | 2.78 | 4.90E-03 |
| | Top 5% vs Rest of population | 2.51 | 0.308 | 1.4 | 4.69 | 2.80E-03 |

* GHS: Logistic regression model adjusted for age, sex, BMI, smoking status, hypertension, CKD and ancestry-informative PCs. UKB (European ancestry): Logistic regression model adjusted for age, sex, BMI, smoking status, hypertension, COPD, ancestry-informative PCs and REGENIE genome-wide predictor.

Figure 5 (cont.)

| Population | PRS Group | Adjusted Odds Ratio* | | | | |
|---|---|---|---|---|---|---|
| | | Estimate | SE | LCI | UCI | P-value |
| UKB SAS | Top 40% vs Rest of population | Number of hospitalized cases too small for analysis (N=49) | | | | |
| | Top 30% vs Rest of population | | | | | |
| | Top 20% vs Rest of population | | | | | |
| | Top 10% vs Rest of population | | | | | |
| | Top 5% vs Rest of population | | | | | |
| UKB AFR | Top 40% vs Rest of population | Number of hospitalized cases too small for analysis (N=74) | | | | |
| | Top 30% vs Rest of population | | | | | |
| | Top 20% vs Rest of population | | | | | |
| | Top 10% vs Rest of population | | | | | |
| | Top 5% vs Rest of population | | | | | |
| PMBB AFR | Top 40% vs Rest of population | Number of hospitalized cases too small for analysis (N=67) | | | | |
| | Top 30% vs Rest of population | | | | | |
| | Top 20% vs Rest of population | | | | | |
| | Top 10% vs Rest of population | | | | | |
| | Top 5% vs Rest of population | | | | | |

* GHS: Logistic regression model adjusted for age, sex, BMI, smoking status, hypertension, CKD and ancestry-informative PCs. UKB (European ancestry): Logistic regression model adjusted for age, sex, BMI, smoking status, hypertension, COPD, ancestry-informative PCs and REGENIE genome-wide predictor.

Figure 5 (cont.)

| Population | PRS Group | Risk of severe disease among COVID-19 cases (N positive and severe / N positive) | | Unadjusted Risk Difference |
|---|---|---|---|---|
| | | Highest GRS group | Rest of Population | |
| GHS EUR | Top 40% vs Rest of population | 4.09 (14/342) | 4.30 (22/512) | -0.20 |
| | Top 30% vs Rest of population | 4.30 (11/256) | 4.18 (25/598) | 0.12 |
| | Top 20% vs Rest of population | 4.68 (8/171) | 4.10 (28/683) | 0.58 |
| | Top 10% vs Rest of population | 2.33 (2/86) | 4.43 (34/768) | -2.10 |
| | Top 5% vs Rest of population | 0.00 (0/43) | 4.44 (36/811) | -4.44 |
| UKB EUR | Top 40% vs Rest of population | 30.32 (218/719) | 23.56 (254/1078) | 6.76 |
| | Top 30% vs Rest of population | 30.24 (163/539) | 24.56 (309/1258) | 5.68 |
| | Top 20% vs Rest of population | 32.22 (116/360) | 24.77 (356/1437) | 7.45 |
| | Top 10% vs Rest of population | 34.44 (62/180) | 25.36 (410/1617) | 9.09 |
| | Top 5% vs Rest of population | 36.67 (33/90) | 25.72 (439/1707) | 10.95 |

* UKB (European ancestry): Logistic regression model adjusted for age, sex, BMI, smoking status, hypertension, COPD, ancestry-informative PCs and REGENIE genome-wide predictor.

Figure 6

| Population | PRS Group | Risk of severe disease among COVID-19 cases (N positive and severe / N positive) | | Unadjusted Risk Difference |
|---|---|---|---|---|
| | | Highest GRS group | Rest of Population | |
| UKB SAS | Top 40% vs Rest of population | 22.22 (8/36) | 12.73 (7/55) | 9.49 |
| | Top 30% vs Rest of population | 25.00 (7/28) | 12.70 (8/63) | 12.30 |
| | Top 20% vs Rest of population | 22.22 (4/18) | 15.07 (11/73) | 7.15 |
| | Top 10% vs Rest of population | 33.33 (3/9) | 14.63 (12/82) | 18.70 |
| | Top 5% vs Rest of population | 40.00 (2/5) | 15.12 (13/86) | 24.88 |
| UKB AFR | Top 40% vs Rest of population | 30.43 (14/46) | 26.09 (18/69) | 4.35 |
| | Top 30% vs Rest of population | 28.57 (10/35) | 27.50 (22/80) | 1.07 |
| | Top 20% vs Rest of population | 30.43 (7/23) | 27.17 (25/92) | 3.26 |
| | Top 10% vs Rest of population | 50.00 (6/12) | 25.24 (26/103) | 24.76 |
| | Top 5% vs Rest of population | 66.67 (4/6) | 25.69 (28/109) | 40.98 |
| PMBB AFR | Top 40% vs Rest of population | 19.70 (13/66) | 14.00 (14/100) | 5.70 |
| | Top 30% vs Rest of population | 18.00 (9/50) | 15.52 (18/116) | 2.48 |
| | Top 20% vs Rest of population | 21.21 (7/33) | 15.04 (20/133) | 6.17 |
| | Top 10% vs Rest of population | 29.41 (5/17) | 14.77 (22/149) | 14.65 |
| | Top 5% vs Rest of population | 44.44 (4/9) | 14.65 (23/157) | 29.79 |

* UKB (European ancestry): Logistic regression model adjusted for age, sex, BMI, smoking status, hypertension, COPD, ancestry-informative PCs and REGENIE genome-wide predictor.

Figure 6 (cont.)

| Population | PRS Group | Adjusted Odds Ratio* | | | | |
|---|---|---|---|---|---|---|
| | | Estimate | SE | LCI | UCI | P-value |
| GHS EUR | Top 40% vs Rest of population | Number of severe cases too small for analysis (N=36) | | | | |
| | Top 30% vs Rest of population | | | | | |
| | Top 20% vs Rest of population | | | | | |
| | Top 10% vs Rest of population | | | | | |
| | Top 5% vs Rest of population | | | | | |
| UKB EUR | Top 40% vs Rest of population | 1.40 | 0.117 | 1.11 | 1.76 | 4.0E-03 |
| | Top 30% vs Rest of population | 1.36 | 0.123 | 1.07 | 1.73 | 1.3E-02 |
| | Top 20% vs Rest of population | 1.45 | 0.139 | 1.11 | 1.91 | 7.1E-03 |
| | Top 10% vs Rest of population | 1.73 | 0.183 | 1.2 | 2.47 | 2.8E-03 |
| | Top 5% vs Rest of population | 1.85 | 0.247 | 1.13 | 2.98 | 1.3E-02 |

* UKB (European ancestry): Logistic regression model adjusted for age, sex, BMI, smoking status, hypertension, COPD, ancestry-informative PCs and REGENIE genome-wide predictor.

Figure 6 (cont.)

| Population | PRS Group | Adjusted Odds Ratio* | | | | |
|---|---|---|---|---|---|---|
| | | Estimate | SE | LCI | UCI | P-value |
| UKB SAS | Top 40% vs Rest of population | Number of severe cases too small for analysis (N=15) | | | | |
| | Top 30% vs Rest of population | | | | | |
| | Top 20% vs Rest of population | | | | | |
| | Top 10% vs Rest of population | | | | | |
| | Top 5% vs Rest of population | | | | | |
| UKB AFR | Top 40% vs Rest of population | Number of severe cases too small for analysis (N=32) | | | | |
| | Top 30% vs Rest of population | | | | | |
| | Top 20% vs Rest of population | | | | | |
| | Top 10% vs Rest of population | | | | | |
| | Top 5% vs Rest of population | | | | | |
| PMBB AFR | Top 40% vs Rest of population | Number of severe cases too small for analysis (N=27) | | | | |
| | Top 30% vs Rest of population | | | | | |
| | Top 20% vs Rest of population | | | | | |
| | Top 10% vs Rest of population | | | | | |
| | Top 5% vs Rest of population | | | | | |

* UKB (European ancestry): Logistic regression model adjusted for age, sex, BMI, smoking status, hypertension, COPD, ancestry-informative PCs and REGENIE genome-wide predictor.

Figure 6 (cont.)

METHODS OF IDENTIFYING SUBJECTS HAVING AN INCREASED RISK OF DEVELOPING A CORONAVIRUS INFECTION AND TREATMENT THEREOF

FIELD

The present disclosure provides methods of treating subjects having or susceptible to having a coronavirus infection, methods of identifying subjects having or susceptible to having an increased risk of developing a coronavirus infection, and methods of diagnosing a coronavirus infection.

BACKGROUND

The severe acute respiratory syndrome coronavirus 2 (SARS-CoV-2) was discovered in Wuhan, China in late 2019 and causes coronavirus disease 2019 (COVID-19). COVID-19 symptoms range from flu-like symptoms such as fever, cough and headaches to respiratory failure, acute immune responses and death, though it is estimated that most infected individuals display few, if any, symptoms. As of September 2020, the disease is responsible for >30 million known infections and >940,000 known deaths worldwide, with a much larger number of cases and deaths likely undetected. Known risk factors include male sex, older age, race, obesity, cardiovascular and kidney disease, chronic obstructive pulmonary disease (COPD), and dementia, among others.

One of the features of COVID-19 infection is that while it could be fatal in some individuals, it could also be entirely asymptomatic in other individuals of comparable age and overall health state. Increased risk of severe disease has been associated with male sex, race, age and obesity, among other risk factors. At present, however, the basis for such disparity is unknown, yet the ability to predict the severity of an individual's symptoms in case of COVID-19 infection would be an invaluable tool for identifying the at-risk population. The ability to identify, monitor, and, if necessary, isolate this population would represent a great advance in managing the current COVID-19 pandemic.

SUMMARY

The present disclosure provides methods of treating a subject with a therapeutic agent that treats or inhibits a coronavirus infection, wherein the subject is suffering from a coronavirus infection or is susceptible to developing a coronavirus infection, the method comprising the steps of: i) determining a polygenic risk score (PRS) for the subject by: a) obtaining or having obtained a biological sample from the subject; and b) performing or having performed a genotyping assay on the biological sample to determine if the subject has a genotype comprising one or more genetic variants associated with susceptibility to developing a coronavirus infection and/or associated with severity of a coronavirus infection; wherein the PRS score reflects the presence or absence of the genetic variants and the homozygosity and heterozygosity of the subject for each of the genetic variants; and ii) when the subject has a PRS score below a desired threshold, then administering or continuing to administer to the subject the therapeutic agent that treats or inhibits the coronavirus infection in a standard dosage amount and/or monitoring the subject for initiation of the coronavirus infection and/or increasing severity of the coronavirus infection; or iii) when the subject has a PRS score above a desired threshold, then administering or continuing to administer to the subject the therapeutic agent that treats or inhibits the coronavirus infection in an amount that is the same as or greater than a standard dosage amount; wherein the presence of a PRS score above the desired threshold indicates the subject has an increased risk of developing the coronavirus infection and/or has an increased risk of developing a severe coronavirus infection.

The present disclosure provides methods of identifying a subject having an increased risk for developing a coronavirus infection or developing a severe coronavirus infection, wherein the method comprises determining a polygenic risk score (PRS) for the subject by: a) obtaining or having obtained a biological sample from the subject; and b) performing or having performed a genotyping assay on the biological sample to determine if the subject has a genotype comprising one or more genetic variants associated with susceptibility to developing a coronavirus infection and/or associated with severity of a coronavirus infection; wherein the PRS score reflects the presence or absence of the genetic variants and the homozygosity and heterozygosity of the subject for each of the genetic variants; when the subject has a PRS score below a desired threshold, then the subject has a decreased risk for developing a coronavirus infection or developing a severe coronavirus infection; and when the subject has a PRS score above a desired threshold, then the subject has an increased risk for developing a coronavirus infection or developing a severe coronavirus infection.

BRIEF DESCRIPTION OF THE FIGURES

The accompanying figures, which are incorporated in and constitute a part of this specification, illustrate several aspects and together with the description serve to explain principles of the present disclosure.

FIG. 1 shows association of high COVID-19 genetic risk score (GRS) with the rate of hospitalization or severe disease in COVID-19 positive patients having one or more established COVID-19 risk factors.

FIG. 2 shows COVID-19 positive and patients and COVID-19 patients requiring hospitalization grouped by age, gender, and identified COVID-19 co-morbidities across several cohorts.

FIG. 3 shows the sample size for different COVID-19 patient categories across several cohorts.

FIG. 4 shows genetic variants shown to associate with risk of COVID-19 in previous GWAS.

FIG. 5 shows risk of hospitalization among COVID-19 positive patients of different ancestries grouped by a GRS and polygenic risk score (PRS).

FIG. 6 shows risk of severe disease among COVID-19 positive patients of different ancestries grouped by a GRS and PRS.

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

As used herein, the terms "treat", "treating", and "treatment" and "inhibit", "inhibiting", and "inhibition" refer to eliciting the desired biological response, such as a therapeutic and prophylactic effect, respectively. In some embodiments, a therapeutic effect comprises one or more of a decrease/reduction in a coronavirus infection, such as a COVID-19 infection, a decrease/reduction in the severity of a coronavirus infection, such as a COVID-19 infection (such as, for example, a reduction or inhibition of development of COVID-19 infection), a decrease/reduction in symptoms and infection-related effects, delaying the onset of symptoms and infection-related effects, reducing the severity of symptoms of infection-related effects, reducing the severity of an acute episode, reducing the number of symptoms and infection-related effects, reducing the latency of symptoms and infection-related effects, an amelioration of symptoms and infection-related effects, reducing secondary symptoms, reducing secondary infections, inhibiting relapse to a coronavirus infection, such as a COVID-19 infection, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of a coronavirus infection, such as a COVID-19 infection development/progression (such as, for example, a complete or partial avoidance/inhibition or a delay), and an increased survival time of the affected host animal, following administration of a therapeutic protocol. Treatment of a coronavirus infection, such as a COVID-19 infection, encompasses the treatment of subjects already diagnosed as having any form of a coronavirus infection, such as a COVID-19 infection, at any clinical stage or manifestation, the delay of the onset or evolution or aggravation or deterioration of the symptoms or signs of a coronavirus infection, such as a COVID-19 infection, and/or inhibiting and/or reducing the severity of a coronavirus infection, such as a COVID-19 infection.

As used herein, the terms "coronavirus infection" or "CoV infection" refer to infection with a coronavirus such as, for example, SARS-CoV-2, MERS-CoV, or SARS-CoV. The term includes coronavirus respiratory tract infections, often in the lower respiratory tract. Symptoms can include high fever, dry cough, shortness of breath, pneumonia, gastro-intestinal symptoms such as diarrhea, organ failure (kidney failure and renal dysfunction), septic shock, and death in severe cases. A severe coronavirus infection can be characterized as having one or more of the following hospitalization, a cytokine storm, shortness of breath, pneumonia, organ failure, septic shock, chest pain or pressure, and/or loss of speech or movement.

As used herein, the term "comorbidity" refers to one or more diseases or conditions in a subject that may enhance the severity of a coronavirus infection or be associated with an increased risk of having a severity coronavirus infection. Comorbidities include, but are not limited to, hypertension, coronary disease, heart failure, type 2 diabetes, chronic kidney disease, asthma, chronic obstructive pulmonary disease (COPD), and Alzheimer's disease.

The present disclosure relates generally to the discovery that stratification of subjects by a COVID-19 polygenic risk score (COVID-PRS or PRS) may be useful in identification of subjects more likely to benefit from treatment with an anti-spike SARS-COV2 monoclonal antibody cocktail (REGN10933+REGN10987; casirivimab and imdevimab), independent of traditional clinical criteria such as older age or other comorbidities (e.g., cardiovascular disease).

The present disclosure provides methods of treating a subject with a therapeutic agent that treats or inhibits a coronavirus infection, wherein the subject is suffering from a coronavirus infection or is susceptible to developing a coronavirus infection. The methods comprise the step of determining a polygenic risk score (PRS) for the subject. In some embodiments, the PRS is determined by obtaining or having obtained a biological sample from the subject, and performing or having performed a genotyping assay on the biological sample to determine if the subject has a genotype comprising one or more genetic variants associated with susceptibility to developing a coronavirus infection and/or associated with severity of a coronavirus infection. The PRS score reflects the presence or absence of the genetic variants and the homozygosity and heterozygosity of the subject for each of the genetic variants. When the subject has a PRS score below a desired threshold, then administering or continuing to administer to the subject the therapeutic agent that treats or inhibits the coronavirus infection in a standard dosage amount and/or monitoring the subject for initiation of the coronavirus infection and/or increasing severity of the coronavirus infection. When the subject has a PRS score above a desired threshold, then administering or continuing to administer to the subject the therapeutic agent that treats or inhibits the coronavirus infection in an amount that is the same as or greater than a standard dosage amount. The presence of a PRS score above the desired threshold indicates the subject has an increased risk of developing the coronavirus infection and/or has an increased risk of developing a severe coronavirus infection.

Genetic factors can play an important role in risk for developing a coronavirus infection, and potentially influence how a subject may respond to drug treatment. PRS combine information from a large number of genetic variants, derived from infection association studies, to create a single composite quantitative measure for each subject which reflects his or her genetically-derived infection risk. A subject with a larger number of risk alleles for a coronavirus infection will have a higher PRS than a subject with fewer alleles. Risk can be evaluated at several thresholds, such as percentiles or standard deviation units of the population distribution. The loci associated with a coronavirus infection risk, such as any of the genetic variants described herein, can be used to stratify subjects by PRS, which would be useful in identification of subjects likely to benefit from treatment with any of the inhibitors described herein, independent of traditional clinical criteria.

PRS calculations may allow for identification of subjects that are most susceptible to developing a coronavirus infection, such as a Covid-19 infection. In addition, PRS calculations may allow for identification of subjects that are most likely to respond to any one of the inhibitors described herein.

In some embodiments, the subject at increased risk of developing a coronavirus infection may be selected on the basis of a PRS, wherein the PRS comprises a weighted sum of a plurality of genetic variants associated with developing a coronavirus infection and is calculated using at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, or at least about 1,000 genetic variants, and if the patient has a PRS above a threshold score, administering any one of the inhibitors described herein and/or practicing any of the separation techniques described herein.

In some embodiments, the disclosure includes in the risk assessment large numbers of alleles, for example, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants from one or more genetic variant databases.

In some embodiments, the present disclosure provides methods of determining a PRS in a subject, the method comprising identifying whether at least about 2 genetic variants, at least about 3 genetic variants, at least about 4 genetic variants, at least about 5 genetic variants, at least about 6 genetic variants, at least about 7 genetic variants, at least about 8 genetic variants, at least about 9 genetic variants, at least about 10 genetic variants, at least about 15 genetic variants, at least about 20 genetic variants, at least about 30 genetic variants, at least about 40 genetic variants, at least about 50 genetic variants, at least about 60 genetic variants, at least about 70 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants from a coronavirus risk database are present in a biological sample from the subject; wherein the presence of a risk allele increases PRS, and wherein the presence of an alternative allele decreases PRS.

In some embodiments, the disclosure provides a method of determining a risk of developing a coronavirus infection in a subject comprising identifying whether the coronavirus genetic variants are present in a biological sample from the subject and calculating a PRS for the subject based on the identified genetic variants, wherein the PRS is calculated by summing the weighted risk score associated with each genetic variant identified. The number of identified genetic variants can be at least about 2 genetic variants, at least about 3 genetic variants, at least about 4 genetic variants, at least about 5 genetic variants, at least about 6 genetic variants, at least about 7 genetic variants, at least about 8 genetic variants, at least about 9 genetic variants, at least about 10 genetic variants, at least about 15 genetic variants, at least about 20 genetic variants, at least about 30 genetic variants, at least about 40 genetic variants, at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants.

In some embodiments, the disclosure provides methods of determining a risk of developing a coronavirus infection in a subject comprising identifying whether the coronavirus genetic variants are present in a biological sample from the subject, calculating a PRS for the subject based on the identified genetic variants, and assigning the subject to a risk group based on the PRS. The PRS may be divided into quintiles, e.g., top quintile, intermediate quintile, and bottom quintile, wherein the top quintile of polygenic scores correspond the highest genetic risk group and the bottom quintile of polygenic scores correspond to the lowest genetic risk group. The number of identified genetic variants can be at least about 2 genetic variants, at least about 3 genetic variants, at least about 4 genetic variants, at least about 5 genetic variants, at least about 6 genetic variants, at least about 7 genetic variants, at least about 8 genetic variants, at least about 9 genetic variants, at least about 10 genetic variants, at least about 15 genetic variants, at least about 20 genetic variants, at least about 30 genetic variants, at least about 40 genetic variants, at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants.

In some embodiments, the disclosure provides methods for selecting subjects or candidates with a risk for developing a coronavirus infection comprising identifying whether at least about 2 genetic variants, at least about 3 genetic variants, at least about 4 genetic variants, at least about 5 genetic variants, at least about 6 genetic variants, at least about 7 genetic variants, at least about 8 genetic variants, at least about 9 genetic variants, at least about 10 genetic variants, at least about 15 genetic variants, at least about 20 genetic variants, at least about 30 genetic variants, at least about 40 genetic variants, at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants associated with coronavirus are present in a biological sample from each subject or candidate; calculating a polygenic risk score PRS for each subject or candidate based on the identified genetic variants; and selecting the subjects or candidates with a desired risk group.

For all coronavirus risk assessments, incorporation of large numbers of genetic variants offers the advantage of increased predictive power. The disclosure further provides risk assessments outlined above incorporating for example, at least 500,000, at least 1,000,000, at least 2,000,000, at least 3,000,000, at least 4,000,000, at least 5,000,000, or at least 6,000,000 genetic variants, or at least 6,500,000 genetic variants, or at least 7,000,000 genetic variants, or at least 8,000,000 genetic variants, or at least 9,000,000 genetic variants, or at least 10,000,000 genetic variants associated with coronavirus.

In some embodiments, the disclosure provides methods for selecting a population of subjects or candidates with a high risk for developing a coronavirus infection comprising identifying whether at least about 2 genetic variants, at least about 3 genetic variants, at least about 4 genetic variants, at least about 5 genetic variants, at least about 6 genetic variants, at least about 7 genetic variants, at least about 8 genetic variants, at least about 9 genetic variants, at least about 10 genetic variants, at least about 15 genetic variants, at least about 20 genetic variants, at least about 30 genetic variants, at least about 40 genetic variants, at least 50 genetic variants, at least 95 genetic variants, at least 100 genetic variants, at least 200 genetic variants, at least 500 genetic variants, at least 1000 genetic variants, at least 2000 genetic variants, at least 5000 genetic variants, at least 10,000 genetic variants, at least 20,000 genetic variants, at least 50,000 genetic variants, at least 75,000 genetic variants, at least 100,000 genetic variants, at least 500,000 genetic variants, at least 1,000,000 genetic variants, at least 2,000,000 genetic variants, at least 3,000,000 genetic variants, at least 4,000,000 genetic variants, at least 5,000,000 genetic variants, or at least 6,000,000 genetic variants, or at least 6,500,000 genetic variants, or at least 7,000,000 genetic variants, or at least 8,000,000 genetic variants, or at least 9,000,000 genetic variants, or at least 10,000,000 genetic variants associated with coronavirus are present in a biological sample from each subject or candidate; calculating a PRS for each subject or candidate based on the identified genetic variants; and selecting the subjects or candidates in the high risk group.

In some embodiments, the number of identified genetic variants is at least 2 genetic variants. In some embodiments, the number of identified genetic variants is at least 3 genetic variants. In some embodiments, the number of identified genetic variants is at least 4 genetic variants. In some embodiments, the number of identified genetic variants is at least 5 genetic variants. In some embodiments, the number of identified genetic variants is at least 6 genetic variants. In some embodiments, the number of identified genetic variants is at least 7 genetic variants. In some embodiments, the number of identified genetic variants is at least 8 genetic variants. In some embodiments, the number of identified genetic variants is at least 9 genetic variants. In some embodiments, the number of identified genetic variants is at least 10 genetic variants. In some embodiments, the number of identified genetic variants is at least 20 genetic variants. In some embodiments, the number of identified genetic variants is at least 20 genetic variants. In some embodiments, the number of identified genetic variants is at least 30 genetic variants. In some embodiments, the number of identified genetic variants is at least 40 genetic variants. In some embodiments, the number of identified genetic variants is at least 50 genetic variants. In some embodiments, the number of identified genetic variants is at least 70 genetic variants. In some embodiments, the number of identified genetic variants is at least 100 genetic variants. In some embodiments, the number of identified genetic variants is at least 500 genetic variants. In some embodiments, the number of identified genetic variants is at least 1,000 genetic variants. In some embodiments, the number of identified genetic variants is at least 2,000 genetic variants. In some embodiments, the number of identified genetic variants is at least 5,000 genetic variants. In some embodiments, the number of identified genetic variants is at least 10,000 genetic variants. In some embodiments, the number of identified genetic variants is at least 20,000 genetic variants. In some embodiments, the number of identified genetic variants is at least 50,000 genetic variants. In some embodiments, the number of identified genetic variants is at least 75,000 genetic variants. In some embodiments, the number of identified genetic variants is at least 100,000 genetic variants. In some embodiments, the number of identified genetic variants is at least 500,000 genetic variants. In some embodiments, the number of identified genetic variants is at least 1,000,000 genetic variants. In some embodiments, the number of identified genetic variants is at least 2,000,000 genetic variants. In some embodiments, the number of identified genetic variants is at least 3,000,000 genetic variants. In some embodiments, the number of identified genetic variants is at least 4,000,000 genetic variants. In some embodiments, the number of identified genetic variants is at least 5,000,000 genetic variants. In some embodiments, the number of identified genetic variants is at least 6,000,000 genetic variants. In some embodiments, the number of identified genetic variants is at least 6,500,000 genetic variants. In some embodiments, the number of identified genetic variants is at least 7,000,000 genetic variants. In some embodiments, the number of identified genetic variants is at least 8,000,000 genetic variants. In some embodiments, the number of identified genetic variants is at least 9,000,000 genetic variants. In some embodiments, the number of identified genetic variants is at least 10,000,000 genetic variants.

In some embodiments, the genetic variants associated with susceptibility to developing a coronavirus infection and/or associated with severity of a coronavirus infection comprise any one or more (or all) of the single nucleotide polymorphisms (SNPs) rs73064425, rs2531743, rs143334143, rs9411378, rs10735079, rs2109069, rs74956615, and rs2236757. In some embodiments, the genetic variant associated with susceptibility to developing a coronavirus infection and/or associated with severity of a coronavirus infection is rs73064425. In some embodiments, the genetic variant associated with susceptibility to developing a coronavirus infection and/or associated with severity of a coronavirus infection is rs2531743. In some embodiments, the genetic variant associated with susceptibility to developing a coronavirus infection and/or associated with severity of a coronavirus infection is rs143334143. In some embodiments, the genetic variant associated with susceptibility to developing a coronavirus infection and/or associated with severity of a coronavirus infection is rs9411378. In some embodiments, the genetic variant associated with susceptibility to developing a coronavirus infection and/or associated with severity of a coronavirus infection is rs10735079. In some embodiments, the genetic variant associated with susceptibility to developing a coronavirus infection and/or associated with severity of a coronavirus infection is rs2109069. In some embodiments, the genetic variant associated with susceptibility to developing a coronavirus infection and/or associated with severity of a coronavirus infection is rs74956615. In some embodiments, the genetic variant associated with susceptibility to developing a coronavirus infection and/or associated with severity of a coronavirus infection is rs2236757. These SNPs were identified by examining the literature for GWAS that included more than 1,000 COVID-19 cases, and having a p value of 5e-8.

In some embodiments of the disclosure, risk assessments comprise the highest weighted PRS scores, including, but not limited to the top 50%, 55%, 60%, 70%, 80%, 90%, or 95% of PRS scores from a patient population.

In some embodiments, the identified genetic variants comprise the highest risk genetic variants or genetic variants with a weighted risk score in the top 10%, top 20%, top 30%, top 40%, or top 50% among genetic variants associated with coronavirus.

In some embodiments, the identified genetic variants comprise the genetic variants having association with developing a coronavirus infection in the top 10%, top 20%, top 30%, top 40%, or top 50% of p-value range. In some embodiments, each of the identified genetic variants comprise the genetic variants having association with developing a coronavirus infection with a p-value of not larger than about $10^{-1}$, about $10^{-2}$, about $10^{-3}$, about $10^{-4}$, about $10^{-5}$, about $10^{-6}$, about $10^{-2}10^{-8}$, about $10^{-8}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with developing a coronavirus infection with p-value of less than $5\times10^{-8}$.

In some embodiments, the identified genetic variants comprise genetic variants having association with developing a coronavirus infection in high-risk patients as compared to the rest of the reference population with odds ratio (OR) of about 1.0 or greater, about 1.5 or greater, about 1.75 or greater, about 2.0 or greater, or about 2.25 or greater for the top up to 50% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, or from about 6.5 to about 7.0. In some embodiments, high-risk patients comprise patients having PRS scores in the top decile, quintile, or tertile in a reference population.

In some embodiments, the identified genetic variants comprise the genetic variants having the highest genetic variant performance in the reference population. In some embodiments, genetic variant performance is calculated with respect to risk for developing a coronavirus infection based on statistical significance, strength of association, and/or a probability distribution.

In some embodiments, genetic variant scores are calculated using PRS calculation methodologies, such as the LDPred method (or variations and/or versions thereof), which is a Bayesian approach to calculate a posterior mean effect for all variants based on a prior (effect size in the prior GWAS) and subsequent shrinkage based on linkage disequilibrium. LDPred creates a PRS using genome-wide variation with weights derived from a set of GWAS summary statistics. See, VilhjáInnsson et al., Am. J. Hum. Genet., 2015, 97, 576-92. In some embodiments, alternate approaches for calculating genetic variant scores may be used, including SBayesR (Lloyd-Jones, L R, world wide web at "biorxiv.org/content/biorxiv/early/2019/01/17/522961.full.pdf"), Pruning and Thresholding (P&T) (Purcell, Nature, 2009, 460, 748-752), and COJO (Yang et al., Nat. Genet., 2012, 44, 369-375). SBayesR is a Bayesian approach is similar to LDPred but allows for more flexibility in the posterior mean effects. Pruning and Thresholding requires that a minimum p-value threshold (p-value associated with the variant from the source data file) and $r^2$ threshold (measure of LD) between variants be specified. P&T identifies the variant with the smallest p-value in each region and then "clumps" under that variant all other variants in the region with an $r^2$ value that is larger than the specified $r^2$. In the PRS, the index variant represents all the variants in the clump (only the index variant is included in the PRS, all other variants are excluded). COJO, or conditional and joint association analysis, is similar conceptually to P&T but incorporates additional variants in a given LD block into the score if they demonstrate independent contribution to a risk for developing a coronavirus infection after conditioning on the index variant.

In some embodiments, genetic variant performance is calculated using the LDPred method, wherein the p value is from about 0.0001 to about 0.5. In some embodiments, genetic variant performance is calculated using the LDPred method, wherein the p value is about 0.5. In some embodiments, genetic variant performance is calculated using the LDPred method, wherein the p value is about 0.1. In some embodiments, genetic variant performance is calculated using the LDPred method, wherein the p value is about 0.05. In some embodiments, genetic variant performance is calculated using the LDPred method, wherein the p value is about 0.01. In some embodiments, genetic variant performance is calculated using the LDPred method, wherein the p value is about 0.005. In some embodiments, genetic variant performance is calculated using the LDpred method, wherein the p value is about 0.001. In some embodiments, genetic variant performance is calculated using the LDPred method, wherein the p value is about 0.0005. In some embodiments, genetic variant performance is calculated using the LDPred method, wherein the p value is about 0.0001.

In some embodiments, the PRS score reflects the presence or absence of the genetic variants and the homozygosity and heterozygosity of the subject for each of the genetic variants and their association with susceptibility to coronavirus infection. In some embodiments, the PRS score reflects the presence or absence of the genetic variants and the homozygosity and heterozygosity of the subject for each of the genetic variants and their association with severity of a coronavirus infection. In some embodiments, the PRS score reflects the presence or absence of the genetic variants and the homozygosity and heterozygosity of the subject for each of the genetic variants and their association with susceptibility to coronavirus infection and severity of a coronavirus infection.

In some embodiments, the susceptibility to developing a coronavirus infection is characterized by having a confirmed infection (i.e., testing positive).

In some embodiments, the severity of a coronavirus infection is characterized by hospitalization, a cytokine storm, shortness of breath, pneumonia, organ failure, septic shock, chest pain or pressure, and/or loss of speech or movement. In some embodiments, the severity of a coronavirus infection is characterized by hospitalization. In some embodiments, the severity of a coronavirus infection is characterized by a cytokine storm. In some embodiments, the severity of a coronavirus infection is characterized by shortness of breath. In some embodiments, the severity of a coronavirus infection is characterized by pneumonia. In some embodiments, the severity of a coronavirus infection is characterized by organ failure. In some embodiments, the severity of a coronavirus infection is characterized by septic shock. In some embodiments, the severity of a coronavirus infection is characterized by chest pain or pressure. In some embodiments, the severity of a coronavirus infection is characterized by loss of speech or movement.

In some embodiments, the PRS score is combined with a comorbidity score. When the subject has a combined PRS score and comorbidity score that is below a desired threshold, then the subject is administered or continued to be administered the therapeutic agent that treats or inhibits the coronavirus infection in a standard dosage amount and/or monitoring the subject for initiation of the coronavirus infection and/or increasing severity of the coronavirus infection. When the subject has a combined PRS score and comorbidity score that is above a desired threshold, then the subject is administered or continued to be administered the therapeutic agent that treats or inhibits the coronavirus infection in an amount that is the same as or greater than a standard dosage amount. The presence of a combined PRS score and comorbidity score that is above the desired threshold indicates the subject has an increased risk of developing the coronavirus infection and/or has an increased risk of developing a severe coronavirus infection. In some embodiments, the subject only has 1 to 5 comorbidities. In some embodiments, the subject only has 1 to 4 comorbidities. In some embodiments, the subject only has 1 to 3 comorbidities. In some embodiments, the subject only has 2 or 3 comorbidities.

In some embodiments, the comorbidity score reflects the presence or absence of, or the severity thereof, comorbidities selected from the group consisting of hypertension, coronary disease, heart failure, type 2 diabetes, chronic kidney disease, asthma, chronic obstructive pulmonary disease (COPD), and Alzheimer's disease, or any combination thereof. In some embodiments, the comorbidity is hypertension. In some embodiments, the comorbidity is coronary disease. In some embodiments, the comorbidity is heart failure. In some embodiments, the comorbidity is type 2 diabetes. In some embodiments, the comorbidity is chronic kidney disease. In some embodiments, the comorbidity is asthma. In some embodiments, the comorbidity is COPD. In some embodiments, the comorbidity is Alzheimer's disease.

Detecting the presence or absence of any of the genetic variants described herein in a biological sample from a subject and/or determining whether a subject has any of the genetic variants described herein can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In any of the embodiments described herein, the nucleic acid molecule can be present within a cell obtained from the subject.

In any of the embodiments described herein, the genotyping assay can be carried out in vitro.

In some embodiments, the genotyping assay comprises sequencing at least a portion of the nucleotide sequence of the genomic nucleic acid molecules in the biological sample. In some embodiments, the genotyping assay comprises sequencing at least a portion of the nucleotide sequence of the mRNA molecules in the biological sample. In some embodiments, the genotyping assay comprises sequencing at least a portion of the nucleotide sequence of the cDNA molecules produced from the mRNA molecules in the biological sample. In some embodiments, the genotyping assay comprises sequencing at least a portion of the nucleotide sequence of one or more nucleic acid molecules encoding LZTFL1, SLC6A20, CCHCR1, ABO, OAS3, DPP9, RAVER1, and/or IFNAR2 and/or regions of nucleic acids adjacent thereto. In some embodiments, the genotyping assay comprises sequencing the entire nucleic acid molecule in the biological sample.

In some embodiments, the genotyping assay comprises: a) amplifying at least a portion of the nucleic acid molecule that encodes LZTFL1, SLC6A20, CCHCR1, ABO, OAS3, DPP9, RAVER1, and/or IFNAR2 and/or regions of nucleic acids adjacent thereto; b) labeling the amplified nucleic acid molecule with a detectable label; c) contacting the labeled nucleic acid molecule with a support comprising an alteration-specific probe; and d) detecting the detectable label.

In some embodiments, the genotyping assay comprises contacting the nucleic acid molecule that encodes encodes LZTFL1, SLC6A20, CCHCR1, ABO, OAS3, DPP9, RAVER1, and/or IFNAR2 and/or regions of nucleic acids adjacent thereto in the biological sample with an alteration-specific probe comprising a detectable label; and detecting the detectable label.

In some embodiments, the nucleic acid molecule is present within a cell obtained from the subject. In some embodiments, the genotyping assay is carried out in vitro.

In any of the embodiments described herein, the coronavirus infection can be Middle East Respiratory Syndrome (MERS), Severe Acute Respiratory Syndrome (SARS), or Coronavirus Disease 2019 (COVID-19). In any of the embodiments described herein, the coronavirus infection can be MERS. In any of the embodiments described herein, the coronavirus infection can be SARS. In any of the embodiments described herein, the coronavirus infection can be COVID-19.

In any of the embodiments described herein, the method can further comprise testing the subject for the presence of SARS-CoV-2.

In any of the embodiments described herein, the therapeutic agent that treats or inhibits the coronavirus infection is lopinavir/ritonavir, chloroquine, hydroxychloroquine, remdesivir, ribavirin, azithromycin, falapirivir, ivermectin, enfuvirtide, amantadine, rimantadine, pleconaril, aciclovir, zidovudine, lamivudine, formivirsen, rifampicin, zanamivir, oseltamivir, peramivir, NP-120 (ifenprodil), favilavir/favipiravir, TMJ2 (TJ003234), TZLS-501, APN01, tocilizumab, galidesivir, sarilumab, SNG001, AmniaBoost, AT-100, colchicine, leronlimab, BPI-002, OYA1, artemisinin, OT-101, Sepsivac, Prezcobix (darunavir and cobicistat), baricitinib, BXT-25, dexamethasone, duvelisib, or an interferon, such as a recombinant interferon, or any combination thereof. In any of the embodiments described herein, the therapeutic agent that treats or inhibits the coronavirus infection is lopinavir/ritonavir. In any of the embodiments described herein, the therapeutic agent that treats or inhibits the coronavirus infection is chloroquine. In any of the embodiments described herein, the therapeutic agent that treats or inhibits the coronavirus infection is hydroxychloroquine. In any of the embodiments described herein, the therapeutic agent that treats or inhibits the coronavirus infection is remdesivir. In any of the embodiments described herein, the therapeutic agent that treats or inhibits the coronavirus infection is ribavirin. In any of the embodiments described herein, the therapeutic agent that treats or inhibits the coronavirus infection is azithromycin. In any of the embodiments described herein, the therapeutic agent that treats or inhibits the coronavirus infection is falapirivir. In any of the embodiments described herein, the therapeutic agent that treats or inhibits the coronavirus infection is ivermectin. In any of the embodiments described herein, the therapeutic agent that treats or inhibits the coronavirus infection is enfuvirtide. In any of the embodiments described herein, the therapeutic agent that treats or inhibits the coronavirus infection is amantadine. In any of the embodiments described herein, the therapeutic agent that treats or inhibits the coronavirus infection is rimantadine. In any of the embodiments described herein, the therapeutic agent that treats or inhibits the coronavirus infection is pleconaril. In any of the embodiments described herein, the therapeutic agent that treats or inhibits the coronavirus infection is aciclovir. In any of the embodiments described herein, the therapeutic agent that treats or inhibits the coronavirus infection is zidovudine. In any of the embodiments described herein, the therapeutic agent that treats or inhibits the coronavirus infection is lamivudine. In any of the embodiments described herein, the therapeutic agent that treats or inhibits the coronavirus infection is formivirsen. In any of the embodiments described herein, the therapeutic agent that treats or inhibits the coronavirus infection is rifampicin. In any of the embodiments described herein, the therapeutic agent that treats or inhibits the coronavirus infection is zanamivir. In any of the embodiments described herein, the therapeutic agent that treats or inhibits the coronavirus infection is oseltamivir. In any of the embodiments described herein, the therapeutic agent that treats or inhibits the coronavirus infection is peramivir. In any of the embodiments described herein, the therapeutic agent that treats or inhibits the coronavirus infection is NP-120 (ifenprodil). In any of the embodiments described herein, the therapeutic agent that treats or inhibits the coronavirus infection is favilavir/favipiravir. In any of the embodiments described herein, the therapeutic agent that treats or inhibits the coronavirus infection is TMJ2 (TJ003234). In any of the embodiments described herein, the therapeutic agent that treats or inhibits the coronavirus infection is TZLS-501. In any of the embodiments described herein, the therapeutic agent that treats or inhibits the coronavirus infection is APN01. In any of the embodiments described herein, the therapeutic agent that treats or inhibits the coronavirus infection is tocilizumab. In any of the embodiments described herein, the therapeutic agent that treats or inhibits the coronavirus infection is galidesivir. In any of the embodiments described herein, the therapeutic agent that treats or inhibits the coronavirus infection is sarilumab. In any of the embodiments described herein, the therapeutic agent that treats or inhibits the coronavirus infection is SNG001. In any of the embodiments described herein, the therapeutic agent that treats or inhibits the coronavirus infection is AmniaBoost. In any of the embodiments described herein, the therapeutic agent that treats or inhibits the coronavirus infection is AT-100. In any of the embodiments described herein, the therapeutic agent that treats or inhibits the coronavirus infection is colchicine. In any of the embodiments described herein, the therapeutic agent that treats or inhibits the coronavirus infection is leronlimab. In any of the embodiments described herein, the therapeutic agent that treats or inhibits the coronavirus infection is BPI-002. In any of the embodiments described herein, the therapeutic agent that treats or inhibits the coronavirus infection is OYA1. In any of the embodiments described herein, the therapeutic agent that treats or inhibits the coronavirus infection is artemisinin. In any of the embodiments described herein, the therapeutic agent that treats or inhibits the coronavirus infection is OT-101. In any of the embodiments described herein, the therapeutic agent that treats or inhibits the coronavirus infection is Sepsivac. In any of the embodiments described herein, the therapeutic agent that treats or inhibits the coronavirus infection is Prezcobix (darunavir and cobicistat). In any of the embodiments described herein, the therapeutic agent that treats or inhibits the coronavirus infection is baricitinib. In any of the embodiments described herein, the therapeutic agent that treats or inhibits the coronavirus infection is BXT-25. In any of the embodiments described herein, the therapeutic agent that treats or inhibits the coronavirus infection is dexamethasone. In any of the embodiments described herein, the therapeutic agent that treats or inhibits the coronavirus infection is duvelisib. In any of the embodiments described herein, the therapeutic agent that treats or inhibits the coronavirus infection is an interferon, such as a recombinant interferon.

In some embodiments, the therapeutic agent that treats or inhibits the coronavirus infection is an anti-inflammatory agent, an antimalarial agent, an antibody or antigen-binding fragment thereof that specifically binds to SARS-CoV-2 viral particles, or COVID-19 vaccines, bromhexine hydrochloride (BHH), 4-(2-aminomethyl)benzenesulfonyl fluoride hydrochloride (AEBSF), nafamostat mesylate, or polyamide. In some embodiments, the antimalarial agent is chloroquine or hydroxychloroquine. In some embodiments, the anti-inflammatory agent is camostat mesylate. In some embodiments, the anti-inflammatory agent is an antibody, such as for example, sarilumab, tocilizumab, or gimsilumab. In some embodiments the COVID-19 vaccine is an inactivated/killed virus vaccine, a live attenuated virus vaccine, or a virus subunit vaccine.

In some embodiments, the therapeutic agent that treats or inhibits the coronavirus infection is the antibody cocktail REGN-COV2. In some embodiments, the therapeutic agent that treats or inhibits the coronavirus infection is the antibody cocktail REGN-COV2, or an antigen-binding fragment of one or both monoclonal antibodies within the antibody cocktail REGN-COV2. In some embodiments, the therapeutic agent that treats or inhibits the coronavirus infection is any of the anti-SARS-COV-2-Spike glycoprotein antibodies, or antigen-binding fragments thereof, disclosed in U.S. Pat. No. 10,787,501, or any combination thereof.

In some embodiments, the therapeutic agent that treats or inhibits the coronavirus infection is the antibody cocktail REGN-COV2 or an anti-IL-6 antibody, or a combination thereof. In some embodiments, the therapeutic agent that treats or inhibits the coronavirus infection is the antibody bamlanivimab (LY-CoV555). In some embodiments, the therapeutic agent that treats or inhibits the coronavirus infection is the antibody cocktail REGN-COV2, an anti-IL-6 antibody, or the antibody bamlanivimab (LY-CoV555), or any combination thereof, or optionally in combination with any other therapeutic agent described herein.

In some embodiments, the dose of the therapeutic agents that treat or inhibit the coronavirus infection can be increased by about 10%, by about 20%, by about 30%, by about 40%, by about 50%, by about 60%, by about 70%, by about 80%, or by about 90% for subjects that are heterozygous or homozygous for one or more of any of the genetic variants described herein (i.e., a greater amount than the standard dosage amount) compared to subjects that do not have any of the genetic variants described herein (who may receive a standard dosage amount). In some embodiments, the dose of the therapeutic agents that treat or inhibit the coronavirus infection can be increased by about 10%, by about 20%, by about 30%, by about 40%, or by about 50%. In addition, the dose of therapeutic agents that treat or inhibit the coronavirus infection in subjects that are heterozygous or homozygous for one or more of any of the genetic variants described herein can be administered more frequently compared to subjects that do not have any one or more of the genetic variants described herein.

Administration of the therapeutic agents that treat or inhibit the coronavirus infection can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit the coronavirus infection can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The present disclosure also provides methods of identifying a subject having an increased risk for developing a coronavirus infection or developing a severe coronavirus infection. The methods comprise determining a PRS for the subject by obtaining or having obtained a biological sample from the subject; and performing or having performed a genotyping assay on the biological sample to determine if the subject has a genotype comprising one or more genetic variants associated with susceptibility to developing a coronavirus infection and/or associated with severity of a coronavirus infection. The PRS score reflects the presence or absence of the genetic variants and the homozygosity and heterozygosity of the subject for each of the genetic variants. When the subject has a PRS score below a desired threshold, then the subject has a decreased risk for developing a coronavirus infection or developing a severe coronavirus infection. When the subject has a PRS score above a desired threshold, then the subject has an increased risk for developing a coronavirus infection or developing a severe coronavirus infection.

In some embodiments, the PRS score reflects the presence or absence of the genetic variants and the homozygosity and heterozygosity of the subject for each of the genetic variants and their association with susceptibility to coronavirus infection. In some embodiments, the PRS score reflects the presence or absence of the genetic variants and the homozygosity and heterozygosity of the subject for each of the genetic variants and their association with severity of a coronavirus infection. In some embodiments, the PRS score reflects the presence or absence of the genetic variants and the homozygosity and heterozygosity of the subject for each of the genetic variants and their association with susceptibility to coronavirus infection and severity of a coronavirus infection. The severity of a coronavirus infection is described herein. Any of the genetic variants described herein, or any combination thereof (such as rs73064425, rs2531743, rs143334143, rs9411378, rs10735079, rs2109069, rs74956615, and r52236757) can be sued to generate the PRS.

In some embodiments, the PRS score is combined with a comorbidity score, and when the subject has a combined PRS score and comorbidity score that is below a desired threshold, then the subject has a decreased risk for developing a coronavirus infection or developing a severe coronavirus infection, and when the subject has a combined PRS score and comorbidity score that is above a desired threshold, then the subject has an increased risk for developing a coronavirus infection or developing a severe coronavirus infection. In some embodiments, the subject only has 1 to 5 comorbidities. In some embodiments, the subject only has 1 to 4 comorbidities. In some embodiments, the subject only has 1 to 3 comorbidities. In some embodiments, the subject only has 2 or 3 comorbidities. The comorbidities can be selected from any of those described herein.

The genotyping assay can be any genotyping assay, such as any of the assays described herein. In some embodiments, the genotyping assay comprises sequencing at least a portion of the nucleotide sequence of the genomic nucleic acid molecules in the biological sample. In some embodiments, the genotyping assay comprises sequencing at least a portion of the nucleotide sequence of the mRNA molecules in the biological sample. In some embodiments, the genotyping assay comprises sequencing at least a portion of the nucleotide sequence of the cDNA molecules produced from the mRNA molecules in the biological sample. In some embodiments, the genotyping assay comprises sequencing at least a portion of the nucleotide sequence of one or more nucleic acid molecules encoding LZTFL1, SLC6A20, CCHCR1, ABO, OAS3, DPP9, RAVER1, and/or IFNAR2 and/or regions of nucleic acids adjacent thereto. In some embodiments, the genotyping assay comprises sequencing the entire nucleic acid molecule in the biological sample.

In some embodiments, the genotyping assay comprises: a) amplifying at least a portion of the nucleic acid molecule that encodes LZTFL1, SLC6A20, CCHCR1, ABO, OAS3, DPP9, RAVER1, and/or IFNAR2 and/or regions of nucleic acids adjacent thereto; b) labeling the amplified nucleic acid molecule with a detectable label; c) contacting the labeled nucleic acid molecule with a support comprising an alteration-specific probe; and d) detecting the detectable label.

In some embodiments, the genotyping assay comprises contacting the nucleic acid molecule that encodes encodes LZTFL1, SLC6A20, CCHCR1, ABO, OAS3, DPP9, RAVER1, and/or IFNAR2 and/or regions of nucleic acids adjacent thereto in the biological sample with an alteration-specific probe comprising a detectable label, and detecting the detectable label.

In some embodiments, the nucleic acid molecule is present within a cell obtained from the subject. In some embodiments, the genotyping assay is carried out in vitro.

In some embodiments, the coronavirus infection is any coronavirus infection described herein.

In some embodiments, the methods further comprise testing the subject for the presence of severe acute respiratory syndrome coronavirus 2 (SARS-CoV-2). In some embodiments, the method further comprises partitioning a subject having an increased risk of developing a coronavirus infection into a high-risk group, and/or isolating and/or monitoring a subject having an increased risk of developing a coronavirus infection.

Determining whether a subject has any of the genetic variants described herein in a biological sample from a subject and/or determining whether a subject has any of the genetic variants described herein can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any of the genetic variants described herein, preliminary processing designed to isolate or enrich the sample for the genomic DNA can be employed. A variety of techniques may be used for this purpose. When detecting the level of any of the variant mRNA molecules, different techniques can be used enrich the biological sample with mRNA. Various methods to detect the presence or level of an mRNA or the presence of a particular variant genomic DNA locus can be used. In some embodiments, the methods described herein can further comprise, for example, obtaining a biological sample from the subject.

In any of the embodiments described herein, the assay or determining step can comprise sequencing the entire nucleic acid molecule. In some embodiments, only a variant genomic nucleic acid molecule is analyzed. In some embodiments, only a variant mRNA molecule is analyzed. In some embodiments, only a variant cDNA molecule obtained from an mRNA is analyzed.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In any of the embodiments described herein, alteration-specific polymerase chain reaction techniques can be used to detect any of the variants described herein. Alteration-specific primers can be used because the DNA polymerase will not extend when a mismatch with the template is present.

In any of the embodiments described herein, the assay or determining step can comprise contacting the biological sample with a primer or probe, such as an alteration-specific primer or alteration-specific probe, that specifically hybridizes to any of the genetic variants described herein and not the corresponding reference nucleic acid molecule under stringent conditions, and determining whether hybridization has occurred.

In some embodiments, the assay or determining step comprises RNA sequencing (RNA-Seq). In some embodiments, the assay or determining step also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify any of the genetic variants described herein. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

The alteration-specific probes or alteration-specific primers can comprise a nucleic acid sequence which is complementary to and/or hybridizes, or specifically hybridizes, to any of the genetic variants described herein, or the complement thereof. In some embodiments, the alteration-specific probes or alteration-specific primers comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 nucleotides. In some embodiments, the alteration-specific probes or alteration-specific primers comprise or consist of at least 15 nucleotides. In some embodiments, the alteration-specific probes or alteration-specific primers comprise or consist of at least 15 nucleotides to at least about 35 nucleotides. In some embodiments, alteration-specific probes or alteration-specific primers hybridize to any of the variant genomic nucleic acid molecules, any of the variant mRNA molecules, and/or any of the variant cDNA molecules under stringent conditions.

In some embodiments, to determine whether any of the nucleic acid molecules within a biological sample comprise any of the genetic variants described herein, the biological sample can be subjected to an amplification method using a primer pair that includes a first primer derived from the 5' flanking sequence adjacent the variant position to produce an amplicon that is indicative of the presence of the variation. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising the variant position, and at least 1, 2, 3, 4, 5, 6, 7, 8, 9, 10, or more nucleotides on each side of the variant positions.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

In any of the embodiments described herein, the isolated alteration-specific probes or alteration-specific primers comprise at least about 15 nucleotides, wherein the alteration-specific probe or alteration-specific primer comprises a nucleotide sequence which is complementary to a portion of a nucleotide sequence of any of the genetic variants described herein. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In any of the embodiments described herein, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to any of the genetic variants described herein. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

In any of the embodiments described herein, the probes (such as, for example, an alteration-specific probe) can comprise a label. In some embodiments, the label is a fluorescent label, a radiolabel, or biotin.

The probes and/or primers (including alteration-specific probes and alteration-specific primers) described herein comprise or consist of from about 15 to about 100, from about 15 to about 35 nucleotides. In some embodiments, the probes and primers described herein (including alteration-specific probes and alteration-specific primers) have a nucleotide sequence that specifically hybridizes to any of the genetic variants disclosed herein, or the complement thereof. In some embodiments, the probes and primers (including alteration-specific probes and alteration-specific primers) specifically hybridize to any of the genetic variants disclosed herein under stringent conditions. In the context of the disclosure "specifically hybridizes" means that the probe or primer (including alteration-specific probes and alteration-specific primers) does not hybridize to a nucleic acid sequence encoding any genomic nucleic acid molecules described herein, any of the reference mRNA molecules described herein, and/or any of the reference cDNA molecules described herein that are not associated with coronavirus.

The isolated nucleic acid molecules (such as probes and primers) can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules (such as probes and primers) can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules (such as probes and primers) disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

In any of the embodiments described herein, the coronavirus infection can be Middle East Respiratory Syndrome (MERS), Severe Acute Respiratory Syndrome (SARS), or Coronavirus Disease 2019 (COVID-19). In any of the embodiments described herein, the coronavirus infection can be MERS. In any of the embodiments described herein, the coronavirus infection can be SARS. In any of the embodiments described herein, the coronavirus infection can be COVID-19.

In any of the embodiments described herein, any of the methods can further comprise testing the subject for the presence of severe acute respiratory syndrome coronavirus 2 (SARS-CoV-2).

In any of the embodiments described herein, any of the methods can further comprise partitioning a subject having an increased risk of developing a coronavirus infection into a high-risk group, and/or isolating and/or monitoring a subject having an increased risk of developing a coronavirus infection. In any of the embodiments described herein, any of the methods can further comprise quarantining a subject having an increased risk of developing a coronavirus infection. In some embodiments, the subject having an increased risk for developing a coronavirus infection is isolated in a quarantine area or ward, or provided a private room, or the infected subject's mobility or access to non-colonized or non-infected subjects or unprotected medical personnel is limited or restricted, and/or dedicated patient care equipment is provided. In some embodiments, when isolation is implemented, use of protective apparel is mandated for medical personal coming in contact with a subject having an increased risk for developing a coronavirus infection. In some embodiments, the presently disclosed methods further comprise monitoring the condition of the subject having an increased risk for developing a coronavirus infection. In some embodiments, monitoring a subject's condition comprises regular testing of the subject for the presence of a coronavirus infection and/or assessing the subject for the presence of symptoms of a coronavirus infection, as described herein, at regular intervals. In some embodiments, the isolation or quarantine measures are implemented for a fixed period of time (such as, for example, two weeks, three weeks, one month, two months, three months, six months, or longer than six months). In some embodiments, the isolation or quarantine measures are maintained for a period of time after a subject no longer tests positive for the presence of a coronavirus infection. In some embodiments, the isolation or quarantine measures are maintained for as long as a subject displays symptoms of a coronavirus infection. In some embodiments, the isolation or quarantine measures are maintained for a period of time after the subject no longer displays symptoms of a coronavirus infection.

In any of the embodiments described herein, when a subject is identified as having an increased risk of developing a coronavirus infection, the subject can be treated with a therapeutic agent that treats or inhibits a coronavirus infection, as described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Genetic Association Studies of COVID-19 Outcomes

A genetic association study of COVID-19 outcomes across individuals with COVID-19 and individuals with no record of SARS-CoV-2 infection were aggregated from three studies and four ancestries. Of the COVID-19 cases, hospitalized patients were more likely to be older, of non-European ancestry and to have pre-existing cardiovascular and lung disease (see, FIG. 2). Using these data, two groups of COVID-19 outcomes were defined: five phenotypes related to disease risk and two phenotypes related to disease severity among COVID-19 cases (see, FIG. 3).

Example 2: Identification of Genetic Variants that Modulate Disease Severity Following SARS-Cov-2 Infection To identify genetic variants that modulate disease severity following SARS-CoV-2 infection, the results for eight independent associations ($r^2<0.05$) with disease risk reported in recent GWAS that included >1,000 cases were replicated (see, FIG. 4) as it was hypothesized that some of these published risk variants could also modulate disease severity. After accounting for multiple testing, six variants had a significant and directionally consistent association with at least one of our five disease risk phenotypes: rs73064425 in LZTFL1 (3p21.31; MAF=7%, OR=1.42, $p=7\times10^{-11}$); rs2531743 near SLC6A20 (3p21.31; MAF=42%, OR=1.06, $p=9\times10^{-4}$); rs143334143 in the MHC (6p21.33; MAF=7%, OR=1.36, $p=6\times10^{-4}$); rs9411378 in ABO (9q34.2; MAF=23%, OR=1.12, $p=6\times10^{-10}$; rs2109069 in DPP9 (19p13.3; MAF=31%, OR=1.06, $p=10^{-4}$); and rs2236757 in IFNAR2 (21q22.1; MAF=29%, OR=1.13, $p=2\times10^{-4}$). The column in FIG. 4 labeled "Reference" refers to Pairo-Castineria et al., "Genetic mechanisms of critical illness in Covid-19", medRxiv, 2020 (world wide web at "medrxiv.org/content/10.1101/2020.09.24.20200048v2.full.pdf+html" and Shelton et al., "Trans-ethnic analysis reveals genetic and non-genetic associations with COVID-19 susceptibility and severity", medRxiv, 2020 (world wide web at "medrxiv.org/content/10.1101/2020.09.04.20188318v1").

Example 3: High COVID-19 GRS Associates with Hospitalization or Severe Disease The present study also aimed to determine whether genetics can help identify individuals at high risk of severe disease, who can be prioritized for prophylactic or therapeutic interventions. The specific focus was on the four variants (in/near LZTFL1, MHC, DPP9 and IFNAR2) with a confirmed association with COVID-19 susceptibility and that also modulate COVID-19 severity. Using these variants, a GRS was created for individuals with COVID-19 and then compared the risk of hospitalization and severe disease between those with a high GRS and all other cases, after adjusting for established risk factors (e.g., age, sex, comorbidities). This analysis showed that a high GRS (top 10%) was strongly associated with risk of hospitalization among individuals with one (OR=3.91, 95% Cl 1.94-8.36, $p=2\times10^{-4}$) or two (OR=5.32, 95% Cl 1.89-19.7, p=0.004) established risk factors (see, FIG. 1). Remarkably, however, there was no association between a high GRS and risk of hospitalization among individuals with many (three or more) risk factors (OR=0.98, 95% Cl 0.47-2.21, p=0.96). In these individuals, risk of hospitalization was very high (about 80%), irrespective of the GRS. Similar results were observed for risk of severe disease (see, FIG. 1). Collectively, these results demonstrate that a GRS calculated using variants associated with disease severity can be used to identify COVID-19 cases at high risk of developing poor disease outcomes, among those who have no or few established risk factors for severe COVID-19. This is important, because many of these individuals might not be prioritized for prophylactic or therapeutic interventions according to current guidelines.

Example 4: Polygenic Risk Scores (PRS) are Predictive of COVID-19 Disease Severity and Risk of Hospitalization in UKB European Ancestry Cohort PRS combine information from a large number of genetic variants, derived from infection association studies, to create a single composite quantitative measure for each individual which reflects his or her genetically derived infection risk. An individual with a larger number of risk alleles for a coronavirus infection will have a higher PRS than an individual with fewer alleles. PRS was calculated for COVID-19 patients and incorporated into the logistic regression model of the COVID-19 outcome for each patient ancestry group in each cohort. High PRS scores were predictive of increased risk of hospitalization in the European ancestry group of UKB cohort, and the predictive power was increased when combined with GRS (see, FIG. 5). Similar results were obtained when this analysis was repeated for risk of severe disease among COVID-19 cases (see, FIG. 6).

Example 5: Use of COVID-19 Polygenic Risk Score (COVID-PRS) for Identification of Subjects for Spike SARS-COV2 Monoclonal Antibody Cocktail Treatment (Prophetic)

COVID-PRS can be evaluated with patients hospitalized with severe or critical COVID-19 (versus matched controls without severe disease) in sarilumab (kevzara) and/or anti-spike clinical trials to further elucidate the genetic drivers associated with risk of severe COVID-19 disease. Furthermore, the COVID-PRS can be evaluated with virologic and clinical efficacy endpoints in patients enrolled in anti-spike SARS-COV2 monoclonal antibody trials (casirivimab and imdevimab). Specifically, the COVID-PRS can be tested with (but not limited to) the following endpoints: presence of antibodies at baseline against the SARS-CoV-2 S protein and/or N protein (i.e., 'SeroAb-Positive' versus 'SeroAb-Negative' status); baseline viral shedding (log 10 copies/nnL), as measured by RT-qPCR in NP swabs; change from baseline in viral shedding endpoints; and change in clinical status from baseline (on a 7-point ordinal scale).

The COVID-PRS may associate with differences in proportions of patients who are SeroAb-Positive and/or differences in viral shedding at baseline. The differences in change from baseline in viral shedding or clinical status across placebo and treatment arms may vary by COVID-PRS strata. These analyses may assess the impact of the PRS on underlying biological mechanisms of COVID-19 disease and identify a subset of patients who may have greater benefit from anti-spike SARS-COV2 monoclonal antibody treatment.

Additional endpoint variables can be optionally utilized in evaluating the COVID-PRS are listed below. Clinical, demographic, laboratory, PK/PD, biomarker/safety endpoints include, but are not limited to: baseline demographic and clinical characteristics; baseline laboratory and biomarker values and change from baseline; concentrations of casirivimab and imdevimab in serum and corresponding PK parameters; immunogenicity ADAs to casirivimab and imdevimab; and proportion of patients with treatment-emergent SAEs.

General efficacy endpoints include, but are not limited to: time-weighted average change from baseline in viral shedding; time to negative RT-qPCR in all tested samples with no subsequent positive RT qPCR in any tested samples; proportion of patients with viral loads below the limit of detection at each visit; proportion of patients with viral loads below the lower limit of quantitation at each visit.

Endpoints for hospitalized patients include, but are not limited to: proportion of patients with at least 1-point or 2-point improvement in clinical status; proportion of patients initiating high-intensity oxygen therapy; days of supplemental oxygen use, high-intensity oxygen therapy, mechanical ventilation; days of hospitalization; proportion of patients re-admitted to hospital after discharge; proportion of patients admitted into an intensive care unit (ICU); days of ICU stay; and all-cause mortality.

Endpoints for ambulatory patients include, but are not limited to: proportion of patients with ≥1 or ≥1 COVID-19-related medically-attended visit; total number of COVID-19-related medically-attended visits; proportion of patients admitted to a hospital due to COVID-19; proportion of patients with ≥1 outpatient or telemedicine visit due to COVID-19; proportion of patients requiring oxygen use, high-intensity oxygen therapy, mechanical ventilation due to COVID-19 (if applicable); days of hospitalization due to COVID-19 (if applicable); proportion of patients with all-cause mortality; time to first onset of symptoms consistent with COVID-19 (asymptomatic cohort only); and duration of symptoms consistent with COVID treatment.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject with a therapeutic agent that treats or inhibits a coronavirus infection, wherein the subject is suffering from a coronavirus infection, the method comprising:

determining a polygenic risk score (PRS) for the subject by:

obtaining or having obtained a biological sample from the subject, wherein the biological sample comprises genomic nucleic acid molecule and/or mRNA; and performing or having performed a genotyping assay on the biological sample to determine if the subject has the single nucleotide polymorphism (SNP) rs2531743 or has rs2531743 and one or more of the SNPs rs73064425, rs143334143, rs9411378, rs10735079, rs2109069, rs74956615, and rs2236757, wherein the PRS reflects: i) the presence or absence of the SNPs and the homozygosity and heterozygosity of the subject for each of the SNPs;

wherein when the subject has a PRS below a desired threshold, administering or continuing to administer to the subject the therapeutic agent that treats or inhibits the coronavirus infection in a standard dosage amount; and wherein when the subject has a PRS above a desired threshold, then administering or continuing to administer to the subject the therapeutic agent that treats or inhibits the coronavirus infection in an amount that is greater than a standard dosage amount.

2. The method of claim 1, wherein:

the PRS is combined with a comorbidity score; and when the subject has a combined PRS and comorbidity score that is below a desired threshold, administering or continuing to administer to the subject the therapeutic agent that treats or inhibits the coronavirus infection in a standard dosage amount; and when the subject has a combined PRS and comorbidity score that is above a desired threshold, then administering or continuing to administer to the subject the therapeutic agent that treats or inhibits the coronavirus infection in an amount that is greater than a standard dosage amount.

3. The method of claim 2, wherein the comorbidity score reflects the presence of, absence of, or severity of a comorbidity comprising hypertension, coronary disease, heart failure, type 2 diabetes, chronic kidney disease, asthma, chronic obstructive pulmonary disease (COPD), or Alzheimer's disease.

4. The method of claim 1, wherein the therapeutic agent that treats or inhibits the coronavirus infection comprises chloroquine, a combination of lopinavir and ritonavir, hydroxychloroquine, remdesivir, ribavirin, azithromycin, falapirivir, ivermectin, enfuvirtide, amantadine, rimantadine, pleconaril, aciclovir, zidovudine, lamivudine, formivirsen, rifampicin, zanamivir, oseltamivir, peramivir, ifenprodil, a combination of favilavir and favipiravir, an anti-GM-CSF antibody, an anti-IL-6 receptor antibody, an angiotensin-converting enzyme-2, tocilizumab, galidesivir, sarilumab, surfactant protein D, colchicine, leronlimab, a bactericidal permeability-increasing protein/lipopolysaccharide-binding protein, sangivamycin, artemisinin, an anti-TGF-β RNA therapeutic agent, a *Mycobacterium* w, a combination of darunavir and cobicistat, baricitinib, cyclophosphamide, dexamethasone, duvelisib, an interferon, a combination of casirivimab and imdevimab, or an anti-IL-6 antibody, or any combination thereof.

5. The method of claim 1, wherein the genotyping assay comprises sequencing at least a portion of the nucleotide sequence of a genomic nucleic acid molecule in the biological sample.

6. The method of claim 1, wherein the genotyping assay comprises sequencing at least a portion of the nucleotide sequence of an mRNA molecule in the biological sample.

7. The method of claim 1, wherein the genotyping assay comprises sequencing at least a portion of the nucleotide sequence of a cDNA molecule produced from an mRNA molecule in the biological sample.

8. The method of claim 1, wherein the genotyping assay comprises sequencing at least a portion of the nucleotide sequence of:

i) at least one nucleic acid molecule encoding LZTFL1, SLC6A20, CCHCR1, ABO, OAS3, DPP9, RAVER1, and/or IFNAR2; and/or ii) at least one nucleic acid region adjacent to the at least one nucleic acid molecule encoding LZTFL1, SLC6A20, CCHCR1, ABO, OAS3, DPP9, RAVER1, and/or IFNAR2.

9. The method of claim 8, wherein the genotyping assay comprises sequencing the entirety of the at least one nucleic acid molecule and/or the at least one nucleic acid region.

10. The method of claim 1, wherein the genotyping assay comprises:

a) amplifying at least a portion of:

i) at least one nucleic acid molecule encoding LZTFL1, SLC6A20, CCHCR1, ABO, OAS3, DPP9, RAVER1, and/or IFNAR2; and/or ii) at least one region adjacent to the at least one nucleic acid molecule encoding LZTFL1, SLC6A20, CCHCR1, ABO, OAS3, DPP9, RAVER1, and/or IFNAR2, thereby providing at least one amplified nucleic acid molecule;

b) labeling the at least one amplified nucleic acid molecule with a detectable label, thereby providing at least one labeled nucleic acid molecule;

c) contacting the at least one labeled nucleic acid molecule with a support comprising an alteration-specific probe, thereby forming a complex of the at least one labeled nucleic acid molecule and the alteration-specific probe; and d) detecting the detectable label of the complex.

11. The method of claim 1, wherein the genotyping assay comprises:

in the biological sample, contacting with an alteration-specific probe:

i) at least one nucleic acid molecule encoding LZTFL1, SLC6A20, CCHCR1, ABO, OAS3, DPP9, RAVER1, and/or IFNAR2; and/or ii) at least one region adjacent to the at least one nucleic acid molecule encoding LZTFL1, SLC6A20, CCHCR1, ABO, OAS3, DPP9, RAVER1, and/or IFNAR2, wherein a complex is formed of the nucleic acid molecule of i) or ii) and the alteration-specific probe, wherein the alteration-specific probe comprises a detectable label; and detecting the detectable label of the complex.

12. The method of claim 1, wherein the genotyping assay is carried out in vitro.

13. The method of claim 1, wherein the coronavirus infection comprises a Middle East respiratory syndrome-related coronavirus infection, a severe acute respiratory syndrome coronavirus 1 (SARS-COV-1) infection, or a severe acute respiratory syndrome coronavirus 2 (SARS-COV-2) infection.

14. The method of claim 1, further comprising testing the subject for the presence of a severe acute respiratory syndrome coronavirus 2 (SARS-COV-2).

15. A method of identifying a subject having an increased risk for developing a coronavirus infection or developing a severe coronavirus infection, the method comprising:

determining a polygenic risk score (PRS) for the subject by:

obtaining or having obtained a biological sample from the subject; and performing or having performed a genotyping assay on the biological sample to determine if the subject has the single nucleotide polymorphism (SNP) rs2531743 or has rs2531743 and one or more of the SNPs rs73064425, rs143334143, rs9411378, rs10735079, rs2109069, rs74956615, and rs2236757;

wherein the PRS reflects: i) the presence or absence of the SNPs and the homozygosity and heterozygosity of the subject for each of the SNPs;

wherein when the subject has a PRS below a desired threshold, the subject has a decreased risk for developing a coronavirus infection or developing a severe coronavirus infection;

wherein when the subject has a PRS above a desired threshold, then the subject has an increased risk for developing a coronavirus infection or developing a severe coronavirus infection.

16. The method of claim 15, wherein:

the PRS is combined with a comorbidity score;

when the subject has a combined PRS and comorbidity score that is below a desired threshold, the subject has a decreased risk for developing a coronavirus infection or developing a severe coronavirus infection; and when the subject has a combined PRS and comorbidity score that is above a desired threshold, the subject has an increased risk for developing a coronavirus infection or developing a severe coronavirus infection.

17. The method according to claim 1, wherein when the subject has a PRS above a desired threshold, the method further comprises partitioning a subject into a high-risk group, isolating the subject, and/or monitoring the subject.

* * * * *